United States Patent [19]
Eppley et al.

[11] Patent Number: 5,916,200
[45] Date of Patent: Jun. 29, 1999

[54] APPARATUS AND METHOD FOR STABILIZATION OF A CRANIAL SHUNT

[75] Inventors: Barry L. Eppley, Indianapolis, Ind.; Jeffrey Duncan, Jacksonville, Fla.; Dean R. Golden, Warsaw, Ind.; Manuel DuJovny, Chicago, Ill.

[73] Assignee: Walter Lorenz Surgical, Inc., Jacksonville, Fla.

[21] Appl. No.: 08/941,836

[22] Filed: Oct. 1, 1997

[51] Int. Cl.[6] ..................................................... A61M 5/32
[52] U.S. Cl. ........................... 604/178; 604/174; 604/175
[58] Field of Search .................................. 604/174, 175, 604/178, 179, 180; 128/DIG. 26

[56] References Cited

U.S. PATENT DOCUMENTS

| | | |
|---|---|---|
| 1,105,105 | 7/1914 | Sherman . |
| 2,238,238 | 4/1941 | Westrope . |
| 2,329,471 | 9/1943 | King . |
| 2,494,229 | 1/1950 | Collison . |
| 2,791,868 | 5/1957 | Viken . |
| 2,846,744 | 8/1958 | Becker . |
| 3,547,114 | 12/1970 | Haboush . |
| 3,779,240 | 12/1973 | Kondo . |
| 4,116,200 | 9/1978 | Braun et al. . |
| 4,219,015 | 8/1980 | Steinmann . |
| 4,360,025 | 11/1982 | Edwards ................................. 604/180 |
| 4,503,848 | 3/1985 | Casper et al. . |
| 4,683,878 | 8/1987 | Carter . |
| 4,793,335 | 12/1988 | Frey et al. . |
| 4,903,691 | 2/1990 | Heini . |
| 4,905,679 | 3/1990 | Morgan . |
| 4,905,680 | 3/1990 | Tunc . |
| 5,087,202 | 2/1992 | Krenkel . |
| 5,201,737 | 4/1993 | Leibinger et al. . |
| 5,346,492 | 9/1994 | Morgan . |
| 5,372,598 | 12/1994 | Luhr et al. . |
| 5,413,577 | 5/1995 | Pollock . |
| 5,468,242 | 11/1995 | Reisberg . |
| 5,578,036 | 11/1996 | Stone et al. ............................... 606/69 |

FOREIGN PATENT DOCUMENTS

| | | |
|---|---|---|
| 290138 | 11/1988 | European Pat. Off. . |
| 291632 | 11/1988 | European Pat. Off. . |
| 433852 | 6/1991 | European Pat. Off. . |

OTHER PUBLICATIONS

Codman & Shurtleff, *Neurosurgical Quality Instruments*, copyright 1965, pp. 10–13.
*For The Few Who Know The Difference*, TiMesh Inc. (1 sheet).
Hans G. Luhr, M.D., Indications for Use of a Microsystem for Internal Fixation in Craniofacial Surgery, J. of Craniofacial Surgery, vol. 1, No. 1, Jan., 1990, pp. 35–52.
Howmedica International, Inc., *Vitallium—Verschiedene Implantate*, p. 54.
Leibinger LP, *Leibinger*, copyright 1995, (1 sheet).
M.E. Mëller, M. Allogöwer and H. Willenegger, *Manual of Internal Fixation*, copyright 1970, pp. 46 and 47.
Translation of G 85 23 003.8 (Germany) Bone Plate, Feb. 1986, Oswald Leibinger Gmbh (Owner).
U. Heim and K.M. Pfeiffer, *Internal Fixation of Small Fractures*, copyright 1974, 1982 and 1988, p. 60.
Walter Lorenz Surgical, Inc., *Surgical Instruments Catalog 5th Edition*, copyright 1993, pp. 10–11.
Walter Lorenz Surgical, Inc., *1.5/2.0mm Combination Titanium Osteosynthesis System*, copyright 1994.

*Primary Examiner*—Wynn Wood Coggins
*Assistant Examiner*—Jennifer R. Sadula
*Attorney, Agent, or Firm*—Harness, Dickey & Pierce, P.L.C.

[57] ABSTRACT

The invention relates to an apparatus and method for stabilization of a shunt relative to a bone. The apparatus includes a body member and a plurality of attachment members forming a part of the body member. Each of the attachment members are operable to receive a bone screw so as to secure the body member to the bone. A plurality of movable fingers are movably attached to the body member. The plurality of movable fingers are adapted to engage and stabilize various size shunts relative to the bone.

33 Claims, 3 Drawing Sheets

APPARATUS AND METHOD FOR STABILIZATION OF A CRANIAL SHUNT

BACKGROUND OF THE INVENTION

1. Field of the Invention

This invention relates generally to an apparatus and method for use in surgical procedures and, more particularly, to an apparatus and method for stabilization of a cranial shunt or catheter.

2. Discussion of the Related Art

Shunts and/or catheters are used in the treatment of increased intracranial pressure, known as hydrocephalus, which can result from infection, injury or brain tumors. The increase in intracranial pressure generally occurs because there is an increase in the accumulation of cerebrospinal fluid within the ventricles of the brain. To relieve the intracranial pressure, it is sometimes necessary to insert a shunt or catheter into a burr hole formed into the skull. This enables the accumulated cerebrospinal fluid to flow out of or be removed from the skull, thereby reducing the intracranial pressure.

Various methods and techniques for stabilizing or fixedly securing the cranial shunt or catheter are known and used in the art. However, use of these various methods and techniques sometimes exhibit several disadvantages.

For example, one method of stabilizing a cranial shunt or catheter is to suture the cranial shunt directly to the skull or to the skin positioned proximate to the burr hole where the shunt is inserted. Alternatively, the portion of the shunt which exits the skull may simply be left alone or stabilized by taping this portion atop the skull. However, the disadvantage with these types of techniques is that the shunt could inadvertently be moved about or be removed from the skull, such as when a patient is moved.

Another stabilizing technique utilizes a cranial burr hole plate having a fixed diameter center hole. This fixed diameter center hole is used to hold a cap which is coupled to the cranial shunt, sometimes known in the art as a silastic cap. The silastic cap in combination with the burr hole plate stabilizes the shunt in a fixed relationship relative to the skull by securing the plate to the skull proximate the burr hole. This technique, however, also exhibits several disadvantages. For instance, because the plate utilizes a fixed diameter center hole, the plate may be used with only a single silastic cap having a size operable to fit within the center hole. Therefore, such a plate will not work with other silastic caps of differing shapes and sizes. This also eliminates the option of using silastic caps produced by various manufacturers because each manufacturer generally uses different shapes and sizes for its particular silastic cap. As a result, should a different size shunt or catheter be required, a unique and different plate would be required for each size shunt or catheter. Furthermore, use of such a plate would also increase surgical costs because multiple plates would have to be stored in a sterile condition and retrievable during the surgical procedure depending on the shunt size required. In addition, because this plate utilizes a fixed center hole, the silastic cap and the shunt must first be secured to the plate prior to insertion of the shunt. Therefore, the option of first inserting the shunt and later using the plate to stabilize the shunt without having to again remove the shunt is eliminated.

Another technique utilizes a generally rectangular shaped plate which is secured relative to the shunt such that the plate traps the shunt against the edge of the burr hole while the plate is secured to the skull. Wire may also be secured about the shunt and fixed to the plate to prevent the shunt from being removed from the burr hole. Here again, this technique has several disadvantages such as potentially creating an abrasion or kinking of the shunt relative to the edge of the burr hole.

What is needed then is an apparatus and method for stabilizing a cranial shunt or catheter which does not suffer from the above-mentioned disadvantages. This will, in turn, reduce the time and cost for such surgical procedures; enable various sizes and shapes of shunts or catheters to be utilized with a single apparatus adapted to be used with all shunt sizes; reduce the potential inadvertent removal of the shunt or catheter; eliminate the need for storing several size plates in order to use various shapes and sizes of shunts or catheters; and provide the option of attaching the apparatus to the shunt before or after the shunt is inserted into the burr hole without having to remove the shunt. It is, therefore, an object of the present invention to provide such an apparatus and method for stabilizing a cranial shunt or catheter.

SUMMARY OF THE INVENTION

In accordance with the teachings of the present invention, an apparatus and method for stabilization of a shunt is disclosed. The apparatus and method is adaptable to stabilize various size shunts relative to a bone. This is basically achieved by utilizing a plurality of movable fingers which are adapted to engage and stabilize the various size shunts.

In one preferred embodiment, an apparatus for stabilization of a shunt relative to a bone is utilized which is operable to be secured to the bone using a plurality of bone screws. This apparatus includes a body member and a plurality of attachment members forming part of the body member. Each of the attachment members is operable to receive one of the bone screws so as to secure the body member to the bone. A plurality of movable fingers are movably attached to the body member such that the plurality of movable fingers are adapted to engage and stabilize various size shunts relative to the bone.

In another preferred embodiment, a method for stabilizing the shunt relative to the bone is disclosed. This method includes an initial step of forming an apparatus for stabilization of a shunt having a body member defining an opening and at least one attachment member forming a part of the body member. A plurality of movable fingers are movably attached to the body and are adapted to engage and stabilize various size shunts relative to the bone. The method also includes drilling a burr hole into the bone at a desired location having a suitable diameter and selecting a shunt having a suitable inner and outer diameter. The method also includes adjusting the movable fingers to resiliently engage the shunt and stabilizing the shunt relative to the bone with the plurality of movable fingers.

Use of the present invention provides an apparatus and method for stabilizing a shunt relative to a bone. As a result, the aforementioned disadvantages associated with the currently available methods and techniques for stabilizing a shunt have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments concerning an apparatus and method for stabilization of a cranial shunt or catheter are merely exemplary in nature and are in no way intended to limit the invention or its application or uses. Moreover, while the present invention is described in detail below with reference to the treatment of increased intracranial pressure or hydrocephalus, it will be appreciated by those skilled in the art that the present invention is clearly not limited to only this type of treatment and may be utilized with various other treatments or for the stabilization of shunts, catheters or other devices at different areas of the body.

Figures 1, 2A, 2B, 2C:
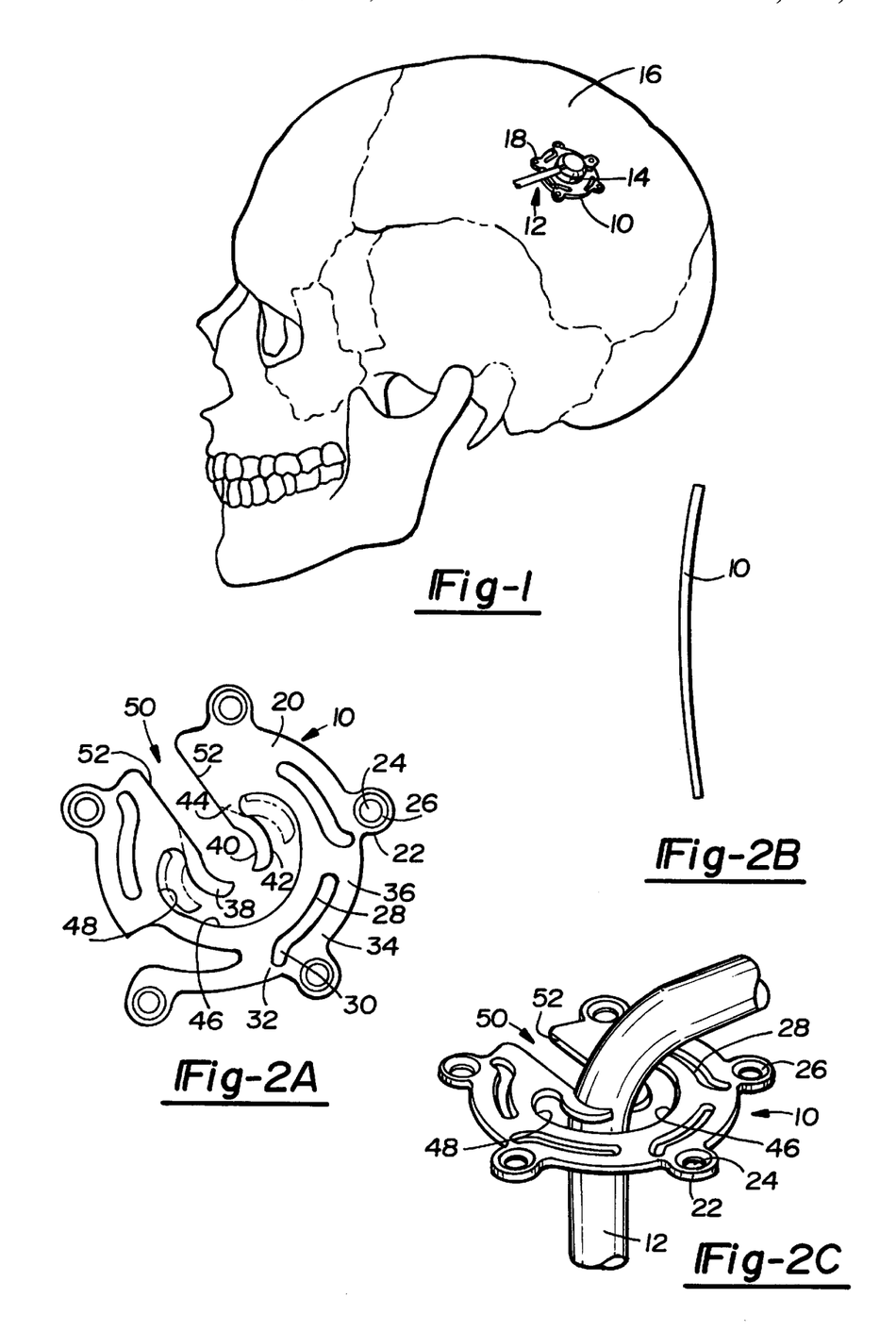
FIG. 1 is a view of an apparatus for stabilization of a cranial shunt or catheter shown in operative association with a human skull.
FIG. 2A is an enlarged front elevational view of the apparatus for stabilization of a cranial shunt or catheter shown in FIG. 1 according to the teachings of a first preferred embodiment of the present invention.
FIG. 2B is a side view of the apparatus for stabilization of a cranial shunt or catheter shown in FIG. 2A.
FIG. 2C is an enlarged perspective view of the apparatus for stabilization of a cranial shunt or catheter of FIG. 2A shown in operative association with a shunt.

Referring to FIG. 1, an apparatus 10 for stabilization of a shunt 12 coupled to a cap 14 is shown fixedly secured to a skull 16. The apparatus 10, hereinafter referred to as a cranial fixation plate 10, stabilizes and fixedly secures the shunt 12 relative to the skull 16 by use of suitable fixation means such as rigid fixation screws 18 positioned substantially concentric around a burr hole (not shown) which receives the shunt 12. As will be appreciated by those skilled in the art and discussed shortly, the cranial fixation plate 10 may be used to secure the shunt 12 having the cap 14 or only the shunt 12 without the cap 14 for use in the treatment of hydrocephalus. In addition, the cranial fixation plate 10 may be used with other types of procedures where it is desirable to stabilize a shunt or catheter at various positions about a patient's body. Further, the term "shunt" or "catheter" as used herein, will be interchangeable and will refer to a tube which is inserted into the body for evacuating or injecting fluids into body cavities or to direct the flow of fluid from one route to another and includes the use of caps or other peripheral components attached to the "shunt" or "catheter."

The cranial fixation plate 10 according to the first preferred embodiment will now be discussed in further detail with reference to FIGS. 2A–2C. The cranial fixation plate 10 includes a body member 20 which is operable to cover at least a portion of the skull 16 and/or the burr hole. The body member 20 is substantially circular in configuration having an outer periphery that is at least partially defined by a center and a radial centerline rotated about the center. The body member 20 may have a spherical convex curve, as shown in FIG. 2B, to generally correspond to the shape of the skull 16. Specifically, it is preferable that the shape of the body member 20 be formed by an arc with a radius of approximately seventy-six (76) millimeters. While the body member 20 is preferably made from commercially pure titanium, it will be understood that any other suitable malleable material may be used which is body compatible, such materials include titanium alloys, chromium-cobolt-molybdenum alloys or other suitable materials.

To provide mounting means for mounting and securing the cranial fixation plate 10 to the skull 16, the cranial fixation plate 10 further includes a plurality of attachment members 22 formed from the body member 20. The attachment members 22 extend radially from the outer periphery of the body member 20 and define bone screw holes 24. The bone screw holes 24 are used to provide means for receiving suitable bone screws (not shown). The bone screw holes 24 are located centrally on the attachment members 22 and serve to secure the attachment members 22 to the skull 16 upon receipt of the bone screws. The bone screws are received in counterbores 26 and are preferably titanium rigid fixation screws or any other suitable screw which is body compatible.

The cranial fixation plate 10 further includes a means for securing the attachment members 22 at a plurality of different positions with respect to the body member 20. This means is set forth in detail in U.S. Ser. No. 08/163,334, filed Dec. 6, 1993, now U.S. Pat. No. 5,578,036, which is hereby incorporated by reference. Briefly, the body member 20 defines a plurality of elongated apertures 28 disposed generally concentric with respect to the body member 20. Each of the elongated apertures 28 includes a curved end portion 30 which is disposed at a distance that is closer to the outer periphery of the body member 20 than the remaining portion of the elongated aperture 28.

The portions of the body member 20 between the curved end portions 30 of the elongated apertures 28 and the outer periphery of the body member 20 are operable to form latch portions 32. The latch portions 32 of the body member 20 serve to secure extension members 34 to the body member 20 until it is desirable to displace an extension member 34 with respect to the body member 20.

When it is desirable to displace an extension member 34, a latch portion 32 of the body member 20 is severed so as to permit the extension member 34 to be moved with respect to the body member 20. This permits the extension member 34 to be displaced by deforming a hinge portion 36 so as to allow the attachment member 22 to be placed in a variety of locations with respect to the body member 20, as shown in FIG. 2A. Because the attachment member 22 may be located at a variety of positions with respect to the body member 20, the attachment member 22 can be suitably located on the skull 16 so as to provide optimum positioning of the body member 20 with respect to the skull 16 and the burr hole, while also providing optimum positioning of the bone screw.

To provide a means for stabilizing the shunt 12 relative to the skull 16, the cranial fixation plate 10 further includes a pair of arcuate-shaped movable fingers 38 formed by the body member 20 and positioned substantially concentric with the center of the body member 20. The arcuate-shaped movable fingers 38 are defined by inner arcuate-shaped sidewalls 40 and outer arcuate-shaped sidewalls 42. The arcuate-shaped movable fingers 38 are attached to the body member 20 at deformable hinge portions 44. The pair of arcuate-shaped movable fingers 38 are positioned within a substantially circular opening 46 defined by the inner periphery of the body member 20. Specifically, the opening 46 is partially defined by the center of the body member 20 and a radial centerline rotated about the center having a radius of about four (4) millimeters. The opening 46 also includes a pair of non-concentric reliefs or recesses 48 which are defined by the body member 20 and substantially conform to the shape of the outer sidewalls 42 of the arcuate-shaped fingers 38.

The inner diameter of the arcuate-shaped fingers 38 defined by the inner sidewalls 40 are preferably preset to receive a cap or a shunt having a diameter of about four (4) millimeters. Should a different size cap or shunt be required, the movable fingers 38 are pivoted at hinge portions 44 by deforming the hinge portions 44, thereby either reducing or enlarging the diameter defined by the inner sidewalls 40, as shown in phantom lines in FIG. 2A. Preferably, the arcuate-shaped movable fingers 38 may be moved to stabilize or secure a cap or shunt having diameters between the range of about one (1) millimeter to about eight (8) millimeters. As the arcuate-shaped fingers 38 are adjusted or moved open to form its maximum diameter, the arcuate-shaped fingers 38 are substantially nestingly received within the reliefs 48 in order to define a substantially complete circular opening 46.

Those skilled in the art will readily observe that if the reliefs 48 are not present within the opening 46, the maximum diameter for receiving a cap or shunt would be greatly decreased. For example, should the opening 46 be partially defined by a center of the body member 20 and a radial centerline rotated about the center having a radius of about five (5) millimeters (i.e. diameter equals ten (10) millimeters), and if the arcuate-shaped fingers 38 are extended until the outer sidewalls 42 strike the inner circumferential edge of the opening 46, the maximum diameter shunt capable of being received would be approximately six (6) millimeters, as opposed to ten (10) millimeters, assuming the width of the fingers 38 are approximately two (2) millimeters.

To provide a means for slidably receiving the shunt or cap after the shunt has been inserted into the burr hole, the cranial fixation plate 10 further includes a channel 50 defined by two substantially parallel sidewalls 52 formed in the body member 20. The arcuate-shaped movable FIGS. 38 extend axially from along the sidewalls 52 defining the channel 50 to slidably receive a portion of the shunt 12. The channel 50 is preset to a width of about three (3) millimeters and is capable of receiving shunts having diameters in the range of about one (1) millimeter to about eight (8) millimeters by simply separating and returning the sidewalls 52 to their original configuration based on the malleable material the plate 10 is formed from.

The channel 50 enables the cranial fixation plate 10 to be utilized after the shunt 12 has already been inserted into the burr hole for later stabilization of the shunt 12. The channel 50 further enables the inner sidewalls 40 of the arcuate-shaped fingers 38 to be brought together relative to one another without the use of the deformable hinges 44 by simply adjusting the attachment members 22 adjacent to each side of the channel 50 closer to one another.

The method of using the present invention will now be described as used in neurosurgical procedures. It is to be understood, however, that the cranial fixation plate 10 may be used with other procedures as well. The cranial fixation plate 10 is first formed as shown in FIGS. 2A and 2B. After the cranial fixation plate 10 has been formed, a burr hole is drilled into the skull 16 at a desired location having a suitable diameter. An appropriate shunt 12 is then selected having a suitable inner and outer diameter. If it is desirable to utilize a silastic cap 14, a suitable silastic cap 14 is selected and attached to the shunt 12. The shunt 12 may then be inserted into the burr hole without attachment of the shunt 12 or the cap 14 onto the plate 10. Alternatively, the shunt 12 or the cap 14 may first be attached to the plate 10 prior to insertion of the shunt 12 into the burr hole.

In some situations, it may be desirable to utilize the shunt 12 without the silastic cap 14 and insert the shunt 12 into the skull 16, via the burr hole, immediately after the burr hole has been formed. Once the shunt 12 is properly positioned within the burr hole, the surgeon can later slide the cranial fixation plate 10 along the portion of the shunt 12 extending from the skull 16 using the channel 50 to slidably receive the shunt 12, as shown in FIG. 2C. Should the movable or bendable arcuate-shaped fingers 38 require adjustment so that the inner sidewalls 40 of the arcuate-shaped fingers 38 resiliently engage and hold the shunt 12, the arcuate-shaped fingers 38 are bent or pivoted at the deformable hinge portions 44. Since the cranial fixation plate 10 is formed from commercially pure titanium which is malleable and flexible, the arcuate-shaped fingers 38 may be deformably moved at deformable hinge portions 44 in order for the fingers 38 to be positioned to resiliently engage various shapes and size shunts.

Once the shunt 12 is secured or stabilized within the arcuate-shaped fingers 38, rigid titanium fixation screws are inserted into the bone screw holes 24 of the attachment members 22. The screws are then fixedly secured to the skull 16 until the heads of the screws (not shown) engage the counterbores 26. Should any of the attachment members 22 be required to be positioned at a different location other than its fixed position, the particular latch portion 32 can be severed and the attachment member 22 moved to its deformable position, via extension member 34.

Figure 3A:
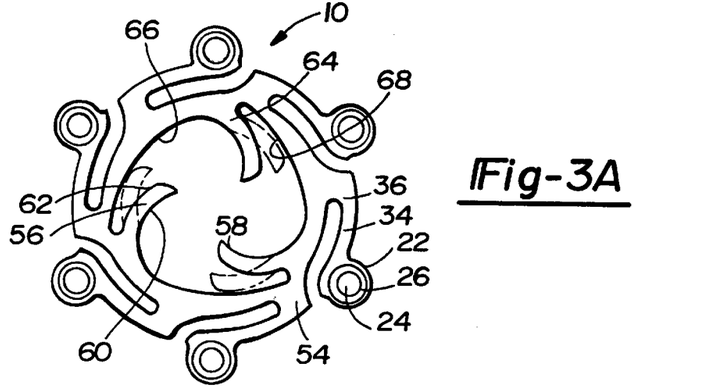
FIG. 3A is an enlarged front elevational view of an apparatus for stabilization of a cranial shunt or catheter according to the teachings of a second preferred embodiment of the present invention.

The second preferred embodiment of the present invention will now be described with reference to FIGS. 3A–3C. In this regard, like reference numerals will be used to identify similar structures as described with respect to the first preferred embodiment of the present invention. The cranial fixation plate 10 according to the second preferred embodiment of the present invention includes a body member 54 also having a substantially circular configuration that is at least partially defined by an outer periphery having a center and a radial centerline rotated about the center. The body member 54 is also convexly curved similar to the body member 20 shown in FIG. 2B. Positioned about the outer periphery of the body member 54 are the attachment members 22 having bone screw holes 24.

To provide means for securing the attachment members 22 at a plurality of different positions with respect to the body member 54, the cranial fixation plate 10 includes the plurality of extension members 34 displaced generally concentric with respect to the body member 54. It should be noted that in this second embodiment, the latch portions 32 of the first embodiment are not shown here and are pre-removed. Accordingly, there is no need to sever the latch portions 32 should it be desirable to position an attachment member 22 at a different position with respect to the body member 54 by deforming a hinge portion 36. One skilled in the art would also readily recognize that either configuration of extension members 34 shown in FIGS. 2A and 3A may be readily interchangeable with respect to each embodiment shown herein.

To provide a means for stabilizing the shunt 12 or the cap 14, the cranial fixation plate 10 includes three arcuate-shaped movable fingers 56 positioned so that the tips 58 of the fingers 56 form an inner diameter region which is substantially concentric with the center of the body member 54. The arcuate-shaped fingers 56 are defined by inner arcuate-shaped sidewalls 60 and outer arcuate-shaped sidewalls 62. The arcuate-shaped movable fingers 56 are attached to the body member 54 at deformable hinge portions 64.

The three arcuate-shaped movable fingers 56 are positioned in an opening 66 defined by the body member 54. The opening 66 is generally concentric with the center of the body member 54 and includes three non-concentric reliefs or recesses 68 defined by the body member 54. The recesses 68 substantially conform to the shape of the outer sidewalls 62 of the arcuate-shaped fingers 56.

The diameter of the opening formed by the tips 58 of the arcuate-shaped fingers 56 is preferably preset to receive a cap or a shunt having a diameter of about 2.5 millimeters. Should a different size cap or shunt be required, the movable fingers 56 can be pivoted or adjusted along hinge portions 64, thereby either reducing or enlarging the diameter defined by the tips 58, shown in phantom lines in FIG. 3A. Preferably, in this embodiment, the arcuate-shaped fingers 56 may be moved or adjusted to stabilize and secure a cap or shunt having a diameter between the range of about one (1) millimeter to about ten (10) millimeters. As the arcuate-shaped fingers 56 are adjusted and moved to form its maximum diameter along the tips 58, the arcuate-shaped fingers 56 are substantially nestingly received within the reliefs 68. This defines a substantially circular opening formed by the inner sidewalls 58 and the circumferential edge of the opening 66.

Figure 3B:
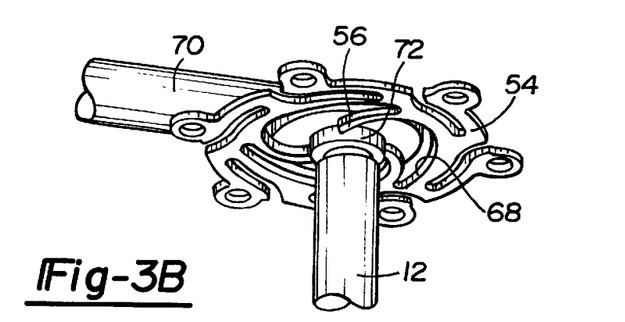
FIGS. 3B–3C are enlarged perspective views of the apparatus for stabilization of a cranial shunt or catheter of FIG. 3 shown in operative association with a shunt utilizing a cap.
Figure 3C:
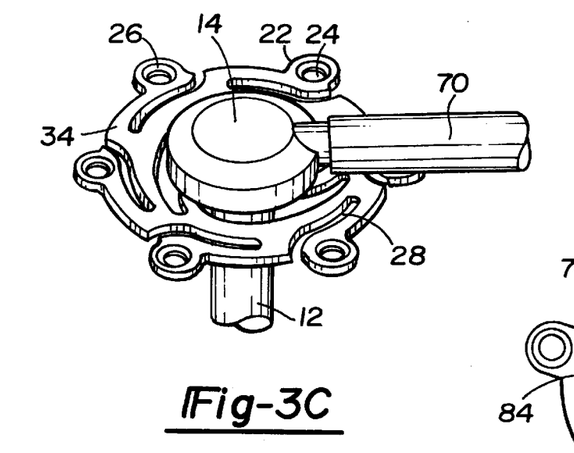

Referring to FIGS. 3B and 3C, the cranial fixation plate 10 of the second preferred embodiment, is shown stabilizing a shunt 12 utilizing a silastic cap 14 coupled to a tube 70. The three movable fingers 56 stabilize the shunt 12 by engaging a ledge portion 72 of the cap 14 with the tips 58. Alternatively, should it be desirable to utilize a shunt 12 without a silastic cap 14, the tips 58 of the fingers would merely engage the shunt 12 similar to that shown in FIG. 2C. It is to be understood that while specific versions of the shunt 12 and cap 14 are shown in FIGS. 2C, 3B and 3C, numerous other conventional and non-conventional shapes and size shunts 12 and silastic caps 14 may be utilized with each preferred embodiment of the present invention.

Figure 4:
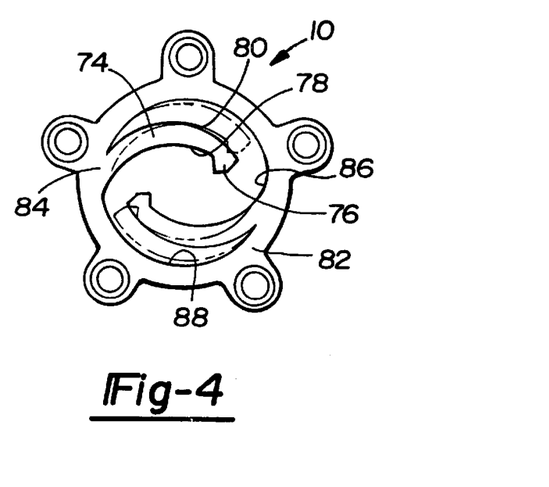
FIG. 4 is an enlarged front elevational view of an apparatus for stabilization of a cranial shunt or catheter according to the teachings of a third preferred embodiment of the present invention.

A third preferred embodiment of the present invention will now be described with reference to FIG. 4. In this regard, like reference numerals are used to identify similar elements as described with respect to the first and second preferred embodiments of the present invention. The cranial fixation plate 10 according to the third preferred embodiment of the present invention functions in a manner similar to that described with respect to the second preferred embodiment of the present invention. However, the third preferred embodiment only includes two arcuate-shaped movable fingers 74 each having teeth 76 for resiliently engaging and gripping a shunt or cap. The arcuate-shaped fingers 74 are defined by inner arcuate-shaped sidewalls 78 and outer arcuate-shaped sidewalls 80. The arcuate-shaped movable fingers 74 are attached to a body member 82 at deformable hinge portions 84. The deformable hinge portions 84 may be narrowed at the connection point to the body member 82 to permit increased ease of deformation and bending at the deformable hinge portions 84.

Here again, the movable fingers 74 are positioned within an opening 86 defined by the body member 82 which is substantially circular in shape having a center and radial centerline rotated about this center. The opening 86 also includes a pair of non-concentric reliefs or recesses 88 defined by the body member 82 which substantially conform to the shape of the outer sidewalls 80 of the arcuate-shaped fingers 74. It should be noted that the body member 82 is shown here without the extension members 34, as set forth in the first and second embodiments. However, those skilled in the art will recognize that the extension members 34 may be incorporated into this third embodiment or alternatively, the extension members 34 may be eliminated from the first or second embodiments.

The inner diameter region of the arcuate-shaped fingers 74 defined by the teeth 76 are preferably preset to receive a cap or a shunt having a diameter of about five (5) millimeters. Should a different size cap or shunt be required, the movable fingers 74 can be pivoted along the hinge portions 84 by deforming the hinge portions 84, which either reduces or enlarges the diameter defined by the teeth 76. Preferably, the arcuate-shaped fingers 74 may be moved to stabilize or secure a cap or shunt having diameters between the range of about one (1) millimeter to about fifteen (15) millimeters. Here again, when the arcuate-shaped fingers 74 are adjusted and moved to form its maximum diameter, the arcuate-shaped fingers 74 are substantially nestingly received within the reliefs 88 in order define a substantial circular opening.

The method of using the second and third preferred embodiments of the present invention will now be described as used in neurosurgical procedures. The cranial fixation plate 10 is first formed as shown in either FIGS. 3A or 4. After the cranial fixation plate 10 has been formed, a burr hole is drilled into the skull 16 at a desired location having a suitable diameter. An appropriate shunt 12 is then selected having a suitable inner and outer diameter. If it is desirable to utilize a silastic cap 14, a suitable silastic cap 14 is selected and attached to the shunt 12. The shunt 12 is then inserted through the opening defined by the movable fingers 56 or 74 and the movable fingers 56 or 74 are then appropriately adjusted to stabilize either the shunt 12 or the silastic cap 14. The shunt 12 is then inserted into the skull 16, via the burr hole. Once the shunt 12 is properly positioned within the burr hole, titanium rigid fixation screws are inserted into the bone screw holes 24 of the attachment members 22. The screws are then fixedly secured to the skull 16 until the heads of the screws engage the counterbores 26.

If either the second or third embodiment are configured to have extension members 34 and it is desirable to position any of the attachment members 22 at a different location relative to its body member, the particular attachment member 22 may be moved to this desirable position prior to securing with the rigid fixation screw. It should be noted that with the embodiments shown in FIGS. 3A and 4, a channel 50 is not provided which eliminates the option of first inserting the shunt 12 without the plate 10 being affixed to the shunt 12, as may be done in some situations. However, if desirable, the second and third embodiments may be adapted to include a channel 50.

The fourth preferred embodiment of the present invention will now be described with reference to FIG. 5. In this regard, like reference numerals will be used to identify similar structures as described with respect to the other preferred embodiments of the present invention. The cranial fixation plate 10 according to the fourth preferred embodiment of the present invention includes a body member formed from a plurality of concentric annular body members 90 each also having a substantially circular configuration that is at least partially defined by an outer periphery having a center and a radial center line located about the center. The body members 90 are also convexley curved similar to the body member 10, shown in FIG. 2B. Positioned about the outer periphery of the first or outermost body member 90 are the attachment members 22 having bone screw holes 24 and counterbores 26. It should be noted that the first body member 90 is shown here without the extension members 34, as set forth in the first and second embodiments. However, those skilled in the art would recognize that the extension members 34 may be incorporated into the first outer body member 90.

To provide a means for stabilizing the shunt 12 or the cap 14, the cranial fixation plate 10 includes three flexible or movable resilient fingers 92 equidistantly positioned around the inner circumference 94 of each body member 90. Each finger 92 includes substantially straight opposing sidewalls 96 and a first end 98 having substantially equal corners 100 and an arcuate tip 102. Each flexible movable finger 92 include a second end 104 integrally coupled to the inner circumference 94 of the body members 90.

Figure 5:
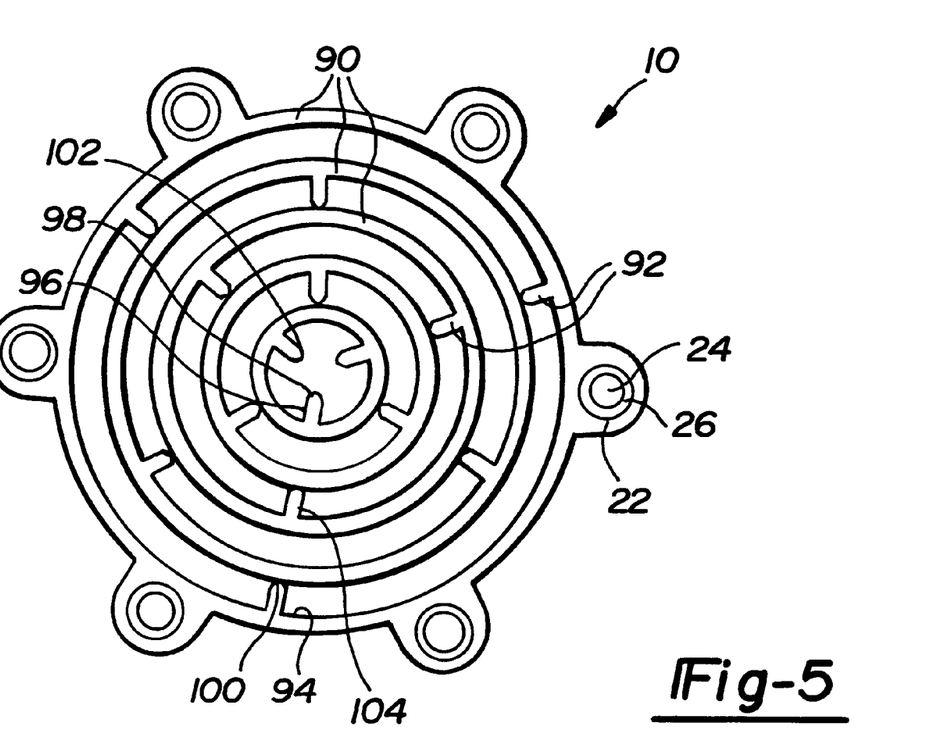
FIG. 5 is an enlarged front elevational view of an apparatus for stabilization of a cranial shunt or catheter according to the teachings of a fourth preferred embodiment of the present invention.

As shown in FIG. 5, the cranial fixation plate 10 includes five substantially annular body members 90 each concentric with one another with each having a slightly smaller diameter from the first outer body member 90. More or less additional body members 90 may also be included with the plate 10. The inner body member 90 or smallest body member 90 has an inner circumferential diameter 94 of about two (2) millimeters with each subsequently enlarged body member 90 increasing in diameter by about two (2) millimeters. Each body member 90 is internally secured or coupled to the next adjacent body member 90 at the arcuate ends 102 of the movable fingers 92.

The diameter of the opening formed by the first set of movable fingers 92 in the innermost body member 90 is preferably preset to receive a cap 14 or shunt 12 having a diameter of about two (2) millimeters. Should a larger size cap 14 or shunt 12 be required, the inner body member 90 and any subsequent adjacent body members 90 may simply be removed from the cranial fixation plate 10 by simply cutting along the appropriate arcuate ends 102 of the appropriate fingers 92. This enables the plate 10 to accommodate for caps 14 or shunts 12 having a diameter between about two (2) millimeters to about eleven (11) millimeters by simply removing the appropriate body members 90 fixed by the fingers 92. The fingers 92 are resiliently movable to engage, secure and stabilize a shunt 12 or cap 14.

The method of using the fourth preferred embodiment of the present invention will now be described as used in neurosurgical procedures. The cranial fixation plate 10 is first formed, as shown in FIG. 5. After the cranial fixation plate 10 has been formed, a burr hole is drilled into the skull 16 at a desired location having a suitable diameter. An appropriate shunt 12 is then selected having a suitable inner and outer diameter. If it is desirable to utilize a silastic cap 14, a suitable silastic cap 14 is selected and attached to the shunt 12.

The cranial fixation plate 10 is then properly sized to accommodate for the shunt 12 or cap 14 selected by merely determining the appropriate body members 90 to be removed from the plate 10. It should be noted that should the shunt 12 or the silastic cap 14 selected not correspond substantially closely to a particular preset diameter of fingers 92 selected, the closest accommodating size should be selected. In this manner, since the resiliently movable fingers 92 are operable to be resiliently moved both up and down or left to right relative to its corresponding body member 90 at ends 104, the movable fingers 92 are operable to resiliently engage and stabilize a shunt 12 or cap 14 that does not substantially correspond to the preset size of the set of three (3) fingers 92 selected.

The shunt 12 is then inserted through the opening defined by the movable fingers 92 and appropriately adjusted to stabilize either the shunt 12 or the silastic cap 14. The shunt 12 is then inserted into the skull 16, via the burr hole. Once the shunt 12 is properly positioned within the burr hole, titanium rigid fixation screws are inserted into the bone screw holes 24 of the attachment members 22. The screws are then fixedly secured to the skull 16 until the heads of the screws engage the counterbores 26. It should be noted that with this embodiment shown in FIG. 5, a channel 50 is not shown which eliminates the option of first inserting the shunt 12 without the plate 10 being affixed to the shunt 12, as may done in some situations. However, if desirable, those skilled in the art, would readily recognize that this fourth embodiment may be adapted to include a channel 50.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. An apparatus for stabilization of a shunt relative to a bone, said apparatus comprising:
   a body member;
   mounting means attached to said body member for mounting said body member to the bone, said mounting means including a plurality of attachment members extending radially from said body member; and
   stabilizing means attached to said body member for stabilizing the shunt relative to the bone, wherein said stabilizing means is movably adapted to be used with various size shunts.

2. The apparatus as defined in claim 1 wherein each of said attachment members defines a bone screw hole operable to receive a bone screw.

3. The apparatus as defined in claim 2 wherein at least one of said attachment members is attached to an extension member attached to said body member, wherein said extension member is operable to be displaced with respect to said body member so as to allow said attachment member to be placed at a plurality of locations with respect to said body member.

4. The apparatus as defined in claim 1 wherein said body member defines a channel operable to slidably receive a portion of the shunt.

5. The apparatus as defined in claim 1 wherein said stabilizing means includes a plurality of movable fingers movably attached to said body member, wherein said plurality of movable fingers are adapted to engage and stabilize various size shunts relative to the bone.

6. The apparatus as defined in claim 5 wherein said plurality of movable fingers include two arcuate-shaped movable fingers.

7. The apparatus as defined in claim 5 wherein said plurality of movable fingers includes three movable fingers.

8. The apparatus as defined in claim 5 wherein said body member defines an opening, said plurality of movable fingers operable to move within said opening, said body member further defining a plurality of reliefs formed into said opening for receiving said plurality of movable fingers upon extending said movable fingers into said plurality of reliefs.

9. An apparatus for stabilization of a shunt relative to a bone, said apparatus comprising:
- a body having a plurality of annular body members each including at least three movable fingers;
- mounting means attached to said body for mounting said body to the bone; and
- stabilizing means attached to said body for stabilizing the shunt relative to the bone, wherein said stabilizing means is movably adapted to be used with various size shunts.

10. The apparatus as defined in claim 9 wherein the plurality of annular body members are concentric with one another and are secured relative to one another with said movable fingers.

11. An apparatus for stabilization of a shunt relative to a bone, said apparatus comprising:
- a body member;
- at least one attachment member operable to secure said body member to the bone; and
- a first arcuate-shaped finger and a second arcuate shaped finger attached to said body member, said first arcuate shaped finger being movable relative to said second arcuate shaped finger, each of said first and second arcuate-shaped fingers having an inner sidewall, said inner sidewalls of said first and second arcuate-shaped fingers defining a substantially circular inner diameter adapted to engage and stabilize various size shunts relative to the bone.

12. An apparatus for stabilization of a shunt relative to a bone, said apparatus being operable to be secured to the bone using a plurality of bone screws, said apparatus comprising:
- a body member;
- a plurality of attachment members extending radially from said body member, each of said attachment members operable to receive at least one of the bone screws so as to secure said body member to the bone; and
- a plurality of fingers attached to said body member, said plurality of fingers including at least one movable finger adapted to engage and stabilize various size shunts relative to the bone.

13. The apparatus as defined in claim 12 wherein said body member includes a first sidewall and a second sidewall, said first and second sidewalls defining a channel operable to slidably receive a portion of the shunt.

14. The apparatus as defined in claim 12 further including at least one extension member coupled to one of said attachment members, wherein said extension member is operable to allow said attachment member to be positioned at a plurality of locations with respect to said body member.

15. The apparatus as defined in claim 12 wherein said body member defines an opening, said plurality of fingers operable to be moved relative to said opening, said body member further defining a plurality of reliefs corresponding to the number of fingers, each of said reliefs operable to substantially nestingly receive a finger.

16. The apparatus as defined in claim 12 wherein each of said fingers includes a deformable hinge operable to be deformed upon moving said finger.

17. The apparatus as defined in claim 12 wherein said plurality of fingers are operable to engage and stabilize a shunt having a diameter of between about one millimeter to about fifteen millimeters.

18. The apparatus as defined in claim 12 wherein said plurality of fingers includes three arcuate-shaped fingers operable to engage and stabilize a shunt having a diameter in the range of between about one millimeter to about ten millimeters.

19. The apparatus as defined in claim 12 wherein said body member has a generally convex shape operable to conform to a shape of a skull.

20. The apparatus as defined in claim 12 wherein said body member includes a plurality of annular body members concentric with one another and coupled together by said plurality of fingers.

21. The apparatus as defined in claim 20 wherein each of said annular body members comprising said body member includes three resiliently movable fingers.

22. An apparatus for stabilization of a shunt relative to a bone, said apparatus comprising:
- a body member having an outer periphery and an inner periphery defining an opening, said body member having a first sidewall and a second sidewall, said first and second sidewalls defining a channel to form a passage extending between said outer periphery to said inner periphery;
- at least one attachment member operable for mounting said body member to the bone; and
- at least one finger operable to stabilize the shunt relative to the bone wherein a portion of the shunt is operable to be slidably received within said channel to pass the shunt from said outer periphery to said inner periphery of said body member.

23. The apparatus as defined in claim 22 wherein said finger is adapted to engage and stabilize various size shunts relative to the bone.

24. The apparatus as defined in claim 23 wherein said apparatus includes two arcuate-shaped movable fingers.

25. The apparatus as defined in claim 24 wherein each of said arcuate-shaped movable fingers axially extends from a sidewall of said body member defining said channel.

26. The apparatus as defined in claim 23 wherein said body member defines a relief formed into said opening, said relief operable to receive said finger.

27. An apparatus for stabilization of a shunt relative to a bone, said apparatus comprising:
- a body having a plurality of separable annular members, said body including an outer annular member and an inner annular member;
- at least one mounting member operable to secure said body to the bone; and
- a plurality of fingers extending from each separable annular member, said plurality of fingers including a plurality of inner fingers extending from said inner annular member of said body, said plurality of inner fingers operable to stabilize the shunt relative to the bone.

28. The apparatus as defined in claim 27 wherein each of said plurality of annular members is secured relative to one another with said plurality of fingers.

29. The apparatus as defined in claim 27 wherein said plurality of separable annular members includes five annular members, whereby said apparatus is operable to stabilize a shunt ranging between a size of about two (2) millimeters to about eleven (11) millimeters.

30. A method for stabilizing a shunt relative to a bone, said method comprising the steps of:
- forming an apparatus for stabilization of the shunt relative to the bone, said apparatus including:
  - (a) a body member defining an opening,
  - (b) a plurality of attachment members extending radially from said body member, and
  - (c) a plurality of movable fingers movably attached to said body member, said plurality of movable fingers operable to be moved relative to said opening and adapted to engage and stabilize various size shunts relative to the bone;

drilling a burr hole into the bone at a desired location having a suitable diameter;

selecting a shunt having a suitable inner and outer diameter;

adjusting said movable fingers to resiliently engage the shunt; and stabilizing the shunt relative to the bone with said plurality of movable fingers.

31. The method as defined in claim 30 wherein the step of selecting a shunt further includes the steps of:

inserting the shunt into the burr hole; and slidably receiving a portion of the shunt with said apparatus while the shunt is inserted into the burr hole.

32. The method as defined in claim 30 wherein the step of stabilizing the shunt relative to the bone further includes the step of inserting the shunt into the burr hole with the movable fingers engaged to the shunt.

33. The method as defined in claim 30 wherein the step of adjusting said movable fingers to resiliently engage the shunt further includes the step of removing appropriate annular members forming said body member by separating said annular members from some of the movable fingers.

* * * * *

UNITED STATES PATENT AND TRADEMARK OFFICE
CERTIFICATE OF CORRECTION

PATENT NO. : 5,916,200  
DATED : June 29, 1999  
INVENTOR(S) : Barry L. Eppley et al.

Page 1 of 1

It is certified that error appears in the above-identified patent and that said Letters Patent is hereby corrected as shown below:

Column 5,
Line 47, "FIGS." should be -- figures --.

Signed and Sealed this

Thirtieth Day of April, 2002

Attest:

JAMES E. ROGAN
*Attesting Officer*  *Director of the United States Patent and Trademark Office*